(12) United States Patent
Lee

(10) Patent No.: US 10,529,209 B2
(45) Date of Patent: Jan. 7, 2020

(54) DUST SENSOR ADOPTING IMPACTOR

(71) Applicant: HITACHI-LG DATA STORAGE KOREA, INC., Seoul (KR)

(72) Inventor: Inwoo Lee, Seoul (KR)

(73) Assignee: HITACHI-LG DATA STORAGE KOREA, INC., Seoul (KR)

( * ) Notice: Subject to any disclaimer, the term of this patent is extended or adjusted under 35 U.S.C. 154(b) by 42 days.

(21) Appl. No.: 16/059,676

(22) Filed: Aug. 9, 2018

(65) Prior Publication Data

US 2019/0080578 A1 Mar. 14, 2019

(30) Foreign Application Priority Data

Sep. 12, 2017 (KR) .................. 10-2017-0116495

(51) Int. Cl.
| | | |
|---|---|---|
| *G08B 17/107* | (2006.01) | |
| *G01N 15/06* | (2006.01) | |
| *G01N 21/53* | (2006.01) | |
| *A47L 9/28* | (2006.01) | |
| *G01N 15/00* | (2006.01) | |
| *G01N 15/02* | (2006.01) | |

(52) U.S. Cl.
CPC .......... *G08B 17/107* (2013.01); *A47L 9/2815* (2013.01); *G01N 21/53* (2013.01); *G01N 15/0255* (2013.01); *G01N 15/06* (2013.01); *G01N 2015/0046* (2013.01); *G01N 2015/0261* (2013.01); *G01N 2015/0693* (2013.01)

(58) Field of Classification Search
CPC ..... G08B 17/107; A47L 9/2815; G01N 21/53; G01N 15/0255; G01N 15/06; G01N 2015/0046; G01N 2015/0261; G01N 2015/0693
See application file for complete search history.

(56) References Cited

U.S. PATENT DOCUMENTS

2007/0269349 A1* 11/2007 Shih ................ G01N 1/2208
73/863.23

* cited by examiner

*Primary Examiner* — Jamil Ahmed
(74) *Attorney, Agent, or Firm* — Birch, Stewart, Kolasch & Birch, LLP

(57) ABSTRACT

The present invention provides a dust sensor comprising an impactor assembly for passing only relatively small particles among particles contained in air; a light emitting unit for radiating light in a path through which the air introduced through the impact assembly passes; and a light receiving unit for receiving light scattered from particles included in the air passing through the path. The impact assembly may comprise an upper case, a first impactor, and a second impactor. The upper case may include an inlet and an outer downward protruding portion. The first impactor may include a central downward depression and a plurality of slots. The second impactor may include an outlet, a central upward protruding portion, a double-bent portion, an outer upward protruding portion and a guide portion.

10 Claims, 8 Drawing Sheets

DUST SENSOR ADOPTING IMPACTOR

This application claims the benefit of priority under 35 U.S.C. § 119(a) to Korean Patent Application No. 10-2017-0116495 filed on Sep. 12, 2017, which is incorporated by reference herein in its entirety.

BACKGROUND

Field

The present invention relates to a structure of a photoelectric dust sensor adopting an impactor.

Related Art

As the population increases and the number of vehicles increases, air pollution becomes worse. There is a growing interest in dust, and air purifier demand is also increasing. For active air cleaning, an air cleaner needs a dust sensor to measure the degree of air pollution, that is, dust concentration in air.

As a dust sensor, a photoelectric dust sensor is mainly used. FIG. 1 conceptually shows the principle of the photoelectric dust sensor sensing dust.

The dust sensor of the photoelectric type comprises an air inlet and an outlet in a housing, passes air flowing from the air inlet through an air passage path, and discharges the air through the air outlet. The dust sensor emits light toward the air passage path via a light emitting unit disposed in the air passage path, collects the light radiated by the light emitting unit and then scattered by dusts included in the air via a light receiving unit disposed in the air passage path, and measures the concentration of dust contained in the air by using an electric signal of the light receiving unit.

If there is little dust or smoke in the air passing through the air passage path, almost all the light emitted from the light emitting unit reaches a light shielding region where the light receiving portion is not disposed, so the amount of light received by the light receiving unit becomes very small. On the other hand, if there is some dust or smoke in the air passing through the air passage path, a part of the light radiated from the light emitting unit is reflected by the dust or smoke in the air passage path and is incident on the light receiving unit, and the light receiving amount of the light receiving unit is increased.

Thus, it is possible to detect the presence/absence of dust or smoke passing through the air passage path based on the fluctuation of the output signal of the light receiving element included in the light receiving unit, and it is possible to detect the concentration of dust or smoke passing through the air passage path based on the output level of the light receiving element.

Meanwhile, there are many different sized particles in the dust. Large particles are caught by filters in the respiratory tract, such as the nares of the nose or bronchus, but small particles, especially nano-particles, do not get caught and accumulate in the lungs and body organs, thereby causing a big problem. Accordingly, there is an increasing need for dust sensors for measuring the concentration of small particles, that is, fine dust.

In order to measure the concentration of fine dust and increase the measurement accuracy thereof, it is necessary to allow only small particles to enter into the dust sensor and prevent the entry of large particles. And, in order to prevent the entry of large particles, it is necessary to provide an impactor at an air intake port of the dust sensor.

However, the conventional impactor used in an expensive dust sensor is complicated in structure, large in size, and expensive, which is not suitable for a consumer or a vehicle, and is difficult to be decomposed and cleaned.

SUMMARY

Accordingly, the present invention has been made in view of such circumstances, and it is an object of the present invention to provide a dust sensor which improves the accuracy of measurement of fine dust.

And, it is another object of the present invention to provide an impactor structure which is employed in a dust sensor and which is small in size, simple in structure, and easy to disassemble and clean.

An impact assembly according to an embodiment of the present invention may comprise: an upper case equipped with an inlet an inlet which is formed through a center of the upper case and through which air is sucked, the upper case including an outer downward protruding portion protruding in a direction in which the air passing through the inlet and formed on an outer portion of a portion where the air that has passed through the inlet escapes; a first impactor including a central downward depression which is formed by sinking a center of a disk-shaped body of the first impactor, the first impactor being provided with a plurality of slots formed along a circumferential direction in an outer periphery of the central downward depression in a radial direction; and a second impactor equipped with an outlet at a center, the second impactor including a central upward protruding portion, a double-bent portion, an outer upward protruding portion and a guide portion, wherein the central upward protruding portion is protruded upward and has a larger outer diameter than the outlet, wherein the double-bent portion is formed by upwardly bending a disk-shaped body of the second impactor at a first position outer than the central upward protruding portion in the radial direction, and then outwardly bending the body of the second impactor, wherein the outer upward protruding portion is protruded upward while being bent from an end portion of the double-bent portion, and wherein the guide portion is protruded downward from a lower surface of the body of the second impactor at a position outer than the central upward protruding portion in the radial direction.

In an embodiment, the impact assembly may further comprise: a first rubber ring disposed between a lower surface of the outer downward protruding portion and an upper surface of the first impactor; and a second rubber ring disposed between a lower surface of the first impactor and an upper surface of the double bent portion.

In an embodiment, an outwardly extending portion of the double bent portion may support the first impactor and the upper case.

In an embodiment, the outer downward protruding portion and the double bent portion may be formed on an outer side of the plurality of slots in the radial direction.

In an embodiment, the outer upward protruding portion may be protruded upward at or above a height at which a surface on which the upper case and the first impactor are in contact is not exposed to outside.

In an embodiment, the outer upward protruding portion may be protruded upward at a position corresponding to outer peripheral end of the upper case and the first impactor in the radial direction.

In an embodiment, an upper portion of the central downward depression may be surrounded by an upper surface of the disk-shaped body of the first impactor to form a first trap, and largest particles among particles contained in the air flowing through the inlet may be contained in the first trap.

In an embodiment, a second trap may be formed between the central upward protruding portion and the double bent portion to hold largest particles among particles contained in the air entering through the plurality of slots.

In an embodiment, the first trap may be formed to be deeper than the second trap.

A dust sensor according to another embodiment of the present invention may comprise: an impactor assembly for passing only relatively small particles among particles contained in air; a light emitting unit for radiating light in a path through which the air introduced through the impact assembly passes; and a light receiving unit for receiving light scattered from particles included in the air passing through the path, wherein the impactor assembly comprises: an upper case equipped with an inlet an inlet which is formed through a center of the upper case and through which air is sucked, the upper case including an outer downward protruding portion protruding in a direction in which the air passing through the inlet and formed on an outer portion of a portion where the air that has passed through the inlet escapes; a first impactor including a central downward depression which is formed by sinking a center of a disk-shaped body of the first impactor, the first impactor being provided with a plurality of slots formed along a circumferential direction in an outer periphery of the central downward depression in a radial direction; and a second impactor equipped with an outlet at a center, the second impactor including a central upward protruding portion, a double-bent portion, an outer upward protruding portion and a guide portion, wherein the central upward protruding portion is protruded upward and has a larger outer diameter than the outlet, wherein the double-bent portion is formed by upwardly bending a disk-shaped body of the second impactor at a first position outer than the central upward protruding portion in the radial direction, and then outwardly bending the body of the second impactor, wherein the outer upward protruding portion is protruded upward while being bent from an end portion of the double-bent portion, and wherein the guide portion is protruded downward from a lower surface of the body of the second impactor at a position outer than the central upward protruding portion in the radial direction.

Accordingly, by adopting an impactor that can be manufactured simply and inexpensively, it is possible to well filter out large sized particles and more precisely measure the concentration of fine dust particles having a small size.

And, by mounting the impactor on the inlet of the dust sensor, external light does not enter the inside of the dust sensor, disturbance caused by the external light can be prevented, and detection accuracy of the dust concentration can be improved.

In addition, since the impactor does not accumulate large particles in the dust sensor, the life of the dust sensor can be extended.

Further, the impactor can be easily disassembled, cleaned and reused, thereby extending the life of the dust sensor and reducing the maintenance cost.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Figure 1:
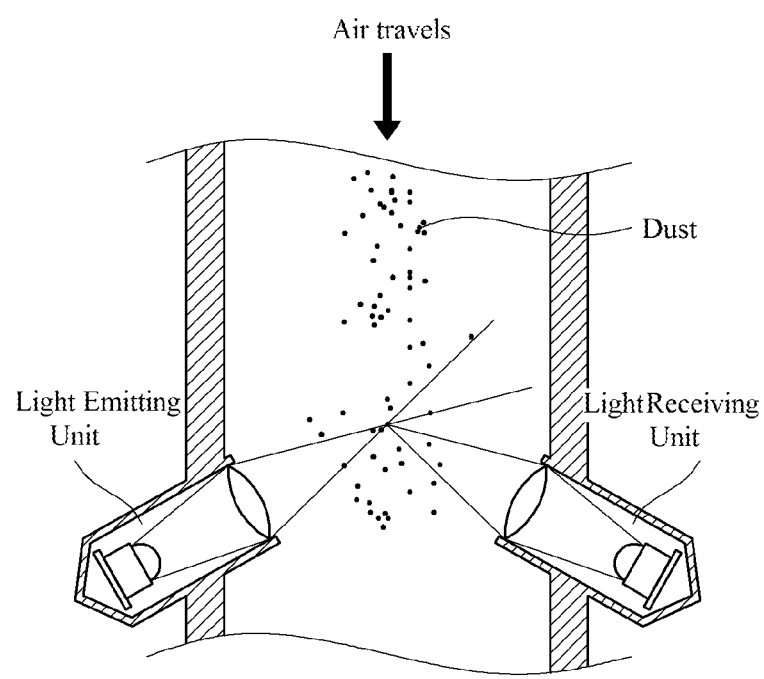
FIG. 1 conceptually shows the principle in which a photoelectric dust sensor senses a dust concentration.

Hereinafter, preferred embodiments of the present invention will be described in detail with reference to the accompanying drawings. Same reference numerals throughout the specification denote substantially identical components. In the following description, a detailed description of known functions and configurations incorporated herein will be omitted when it may make the subject matter of the present invention rather unclear.

The photoelectric type dust sensor is a device of measuring dust density by receiving light scattered from fine particles such as dust contained in air via a light receiving element and outputting an electric signal.

The impactor employed in the dust sensor prevents large particles from entering the dust sensor, limits the size of particles introduced into the dust sensor, and accurately measures the concentration of fine dust.

Figure 2:
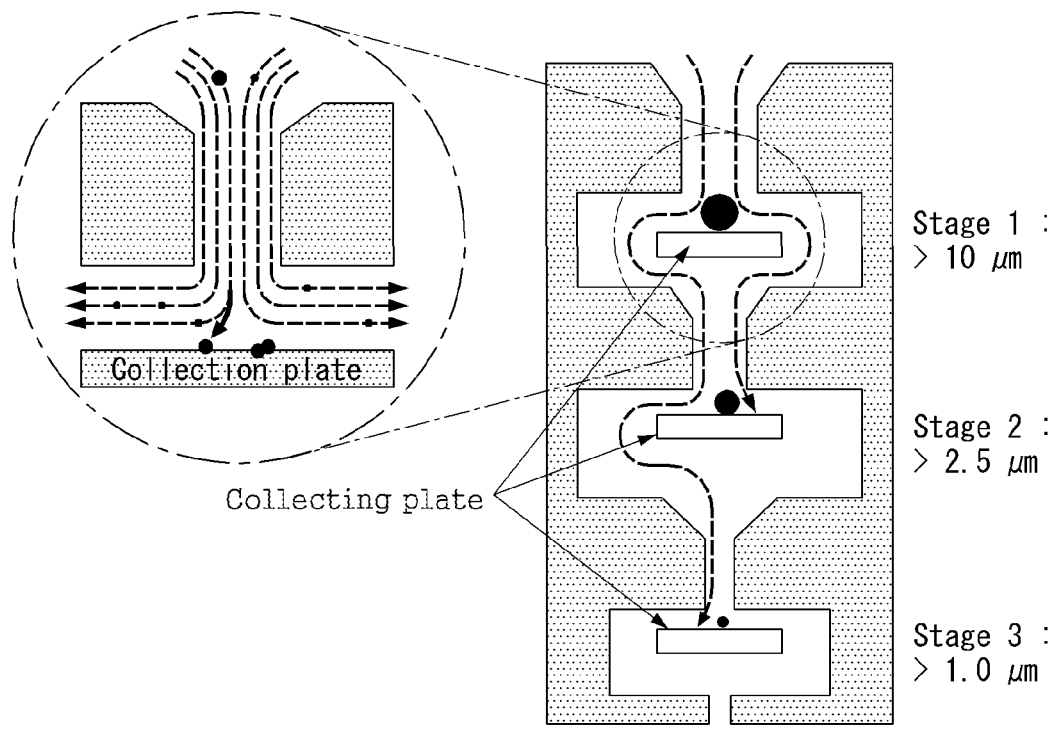
FIG. 2 shows the assembly structure of a multi-stage impactor used in a conventional industrial dust sensor.

FIG. 2 shows the assembly structure of a multi-stage impactor used in a conventional industrial dust sensor, and the impactor of FIG. 2 is a third stage impactor.

Each stage in the impactor assembly is provided with a nozzle which air comes in through, a collection substrate on which the air strikes, and a space (chamber) through which the air bouncing the collecting substrate bypasses in order for the air to proceed to the next stage.

Dust particles entering through the nozzle collide with the collecting substrate and branch to the left and right of the collecting substrate by air pressure. Small particles pass between the collecting substrate and the end sides of the nozzle by air pressure after impacting the collecting substrate. However, large particles move left and right by air pressure after hitting the collecting substrate, but do not move far enough, stay on the collecting substrate surface and fail to pass between the collecting substrate and the end sides of the nozzle.

In a first stage, large particles, for example, 10 um or more of particles collide against and are trapped on the collection substrate. In a second stage, particles of medium size, for example, 2.5 um or more of particles collide against and are trapped on the collection substrate. And, in a third stage, small particles, for example, 1.0 um or more of particles collide against and are trapped on the collection substrate.

To this end, as stages advance, the width of the nozzle into which air enters and the distance between the end sides of the nozzle and the collecting substrate are reduced.

If the width of the nozzle into which air enters and the distance between the end sides of the nozzle and the collecting substrate are increased, the pressure of the air decreases, so larger particles among the dust particles hitting the collecting substrate do not pass between the nozzle and the collecting substrate, but smaller particles pass between the nozzle and the collecting substrate and proceed to a next stage.

However, the impactor assembly of FIG. 2 is complicated in structure, large in size, and expensive in price, so it is not suitable for consumer electronic devices or automobiles. And, the impactor assembly of FIG. 2 has a problem in that it is difficult to reassemble it after decomposing and washing it because the position of the collecting substrate must be precisely adjusted at each stage.

Figure 3:
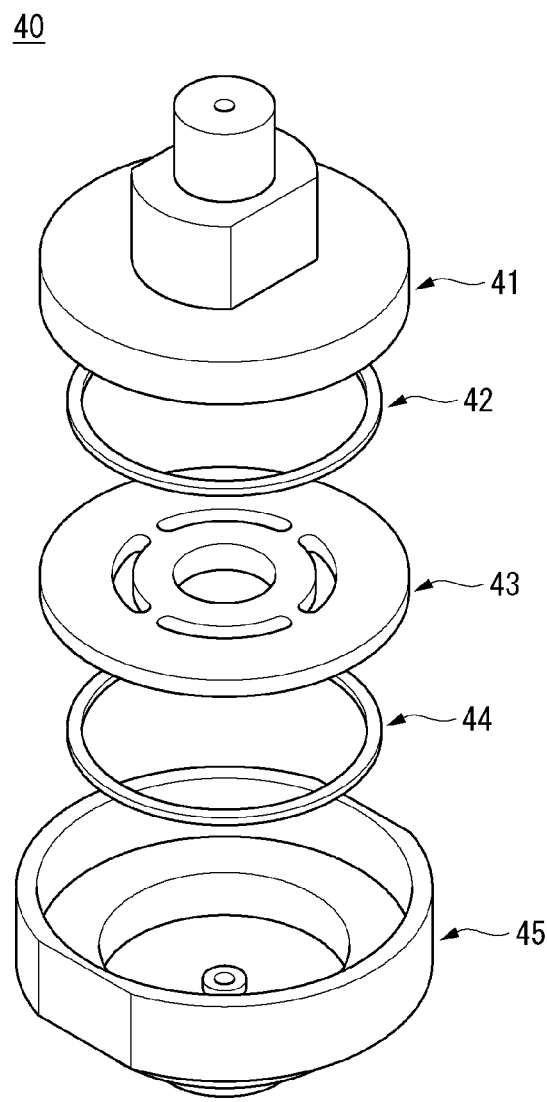
FIG. 3 is an disassembled perspective view of an impactor assembly according to the present invention.

FIG. 3 is a disassembled perspective view of an impactor assembly according to the present invention, and the impactor assembly according to the present invention may be configured in two stages.

The impactor assembly 40 of FIG. 3 may comprise an upper case 41 through which air comes in, a first impactor 43 with which the dust particles contained in the air passing through the inlet of the upper case 41 collide, in which a part or large particles remain and through which small particles pass, a second impactor 45 in which a part among the dust particles passing through the first impactor 43 remain and which passes smaller particles to output to a sensing unit, a first rubber ring 42 disposed between the upper case 41 and the first impactor 43, and a second rubber ring 44 disposed between the first impactor 43 and the second impactor 45.

The upper case 41, the first impactor 43, and the second impactor 45 may be made of plastic injection.

FIGS. 4A to 4D are cross-sectional views of major components constituting the impactor assembly according to the present invention and an assembled cross-sectional view.

Figure 4A:
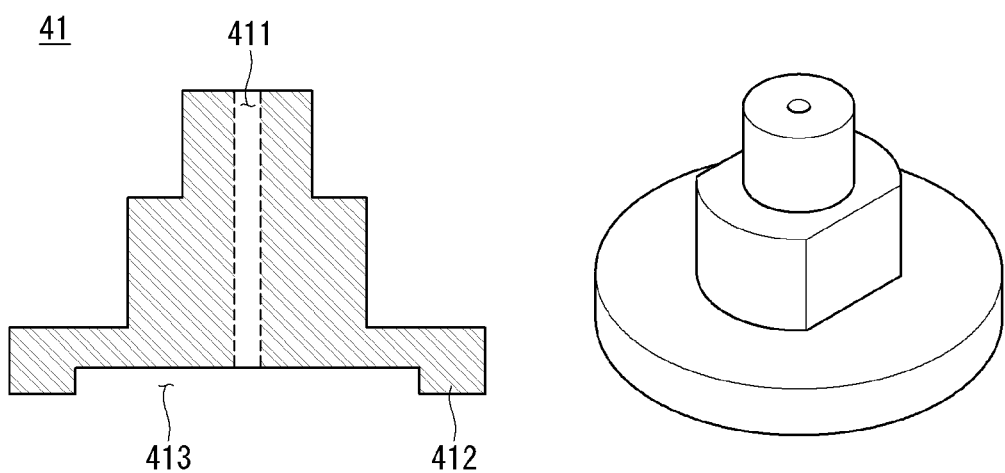
FIGS. 4A to 4D are cross-sectional views of major components constituting the impactor assembly according to the present invention and a their assembled cross-sectional view.

The left drawing of FIG. 4A shows a cross section of the upper case 41. An inlet 411 through which air is sucked is formed at the center and penetrates from top to bottom. An outer downward protruding portion 412 protruding downward, that is, in a direction in which air advances may be formed on the outer portion of the portion where the air that has passed through the inlet 411 escapes.

A lower space 413 through which particles contained in the air are spread is formed, by the outer downward protruding portion 412, on the lower surface of the upper case 41, that is, a portion where the air that has passed through the inlet 411 passes out.

In FIG. 4A, the upper outer periphery of the upper case 41 has a two-step shape. However, this is to make the upper case 41 easier to hold and to reduce the weight and volume when disassembling the impactor assembly 40. There is no significant contribution to the function of the impactor so other shapes are possible.

Figure 4B:
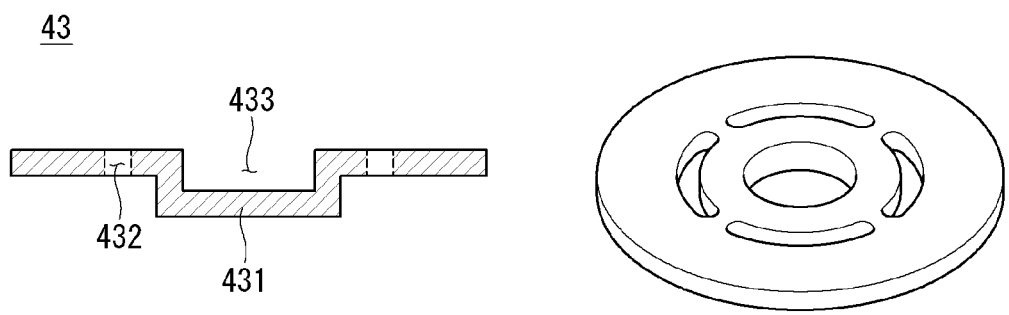

The left drawing of FIG. 4B shows a cross section of the first impactor 43. The center portion of a disc is depressed downwardly and four slots are formed around the circumference of the disc which is not depressed downwardly. The number of slots of the first impactor 43 is not limited to 4.

The first impactor 43 may comprise a central downward depression 431 and a plurality of slots 432 in order to keep large particles out of the particles contained in the air that has passed through the upper case 41. The center of the disk (the body of the first impactor) sinks in a downward direction, i.e., the direction in which the air passes through the inlet 411 of the upper case 41 to form the central downward depression 431. In order for particles of small size among the air particles colliding with the upper surface of the central downward depression 431 to pass through the body of the first impactor 43, a plurality of slots 432 are formed along a circumferential direction (tangential direction) in the outer periphery of the central downward depression 431 in a radial direction (radial direction).

The upper portion of the central downward depression 431 is surrounded by an upper surface of the disk which is the body of the first impactor 43 to form a first trap 433. The particles contained in the air that has passed through the upper case 41 may collide with the upper surface of the central downward depression 431 so that the first trap 433 may contain particles of a larger size among the particles.

Particles having a relatively small size among the particles that have passed through the upper case 41 and hit the upper surface of the central downward depression 431 flow out downward through a plurality of slots 413 formed on the outer periphery of the central downward depression 431.

If the height difference between the upper surface of the central downward depression 431 and the upper surface of the disk which is the body of the first impactor 43 is large, the number of particles is increased, so the particles stay from larger particles to relatively smaller particles. The smaller the height difference is, the smaller the particles contained in the first trap 433 are, and only large particles remain.

the outer downward protruding portion 412 of the upper case 41 is formed radially outwardly of the slots 432 of the first impactor 43 so that the lower space 413 which is formed in the lower portion of the upper case 41 covers the central downward depression 431 and the slots 432 of the first impactor 43.

Figure 4C:
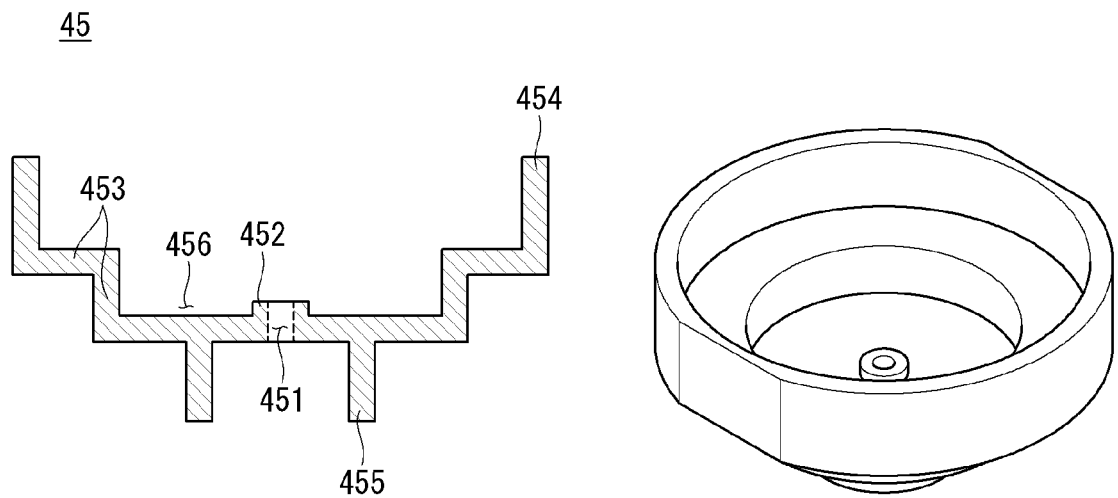

The left drawing of FIG. 4C shows a cross section of the second impactor 45.

The second impactor 45 may comprise an outlet 451, a central upward protruding portion 452, a double-bent portion 453, an outer upward protruding portion 454, and a guide portion 455 in order to keep relatively larger particles among the particles contained in the air that has passed through the first impactor 43. The outlet 451 is disposed at the center of the second impactor 45 in order to vent air. The central upward protruding portion 452 is protruded upward at the center of the upper surface of a disk (the body of the second impactor) and has a larger outer diameter than the outlet 451. The double-bent portion 453 is upwardly bent from the disk which is the body of the second impactor and then again bent outwardly in order to support the first impactor 43. The outer upward protruding portion 454 is protruded upward while being bent from the end portion of the double-bent portion 453 in order for the outer downward protruding portion 412 of the upper case 41 and the outer periphery of the first impactor 43 to be sealed without being exposed. The guide portion 455 is protruded downward from the lower surface of the disk, that is the body of the second impactor, in order to guide the air coming out from the outlet 451 to travel downward.

The upper portion of the second impactor between the central upward protruding portion 452 and the double-bent portion 453 forms a second trap 456 to contain relatively larger particles among the particles contained in the air passing through the first impactor 43. Relatively smaller particles among the particles contained in the air passing through the first impactor 43 pass over the central upward protruding portion 452 and out through the outlet 451.

The outlet 451 of the second impactor may be smaller than the inlet 411 of the upper case 41 in their diameters.

Figure 4D:
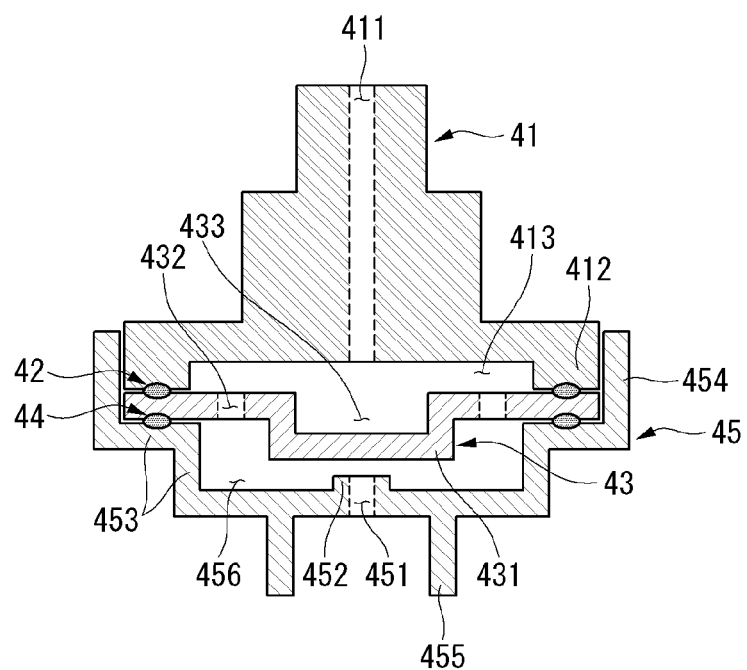

FIG. 4D is a cross section of an assembly combining major components constituting the impactor assembly.

The outer downward protruding portion 412 of the upper case 41 is located further outward than the slots 432 of the first impactor 43, and the double-bent portion 453 of the second impactor 45 is also located further outward than the slots 432 of the first impactor 43.

A portion of the second impactor 45 extending outwardly from the double-bent section 453 supports the first impactor 43 and the upper case 41.

The first rubber ring 42 is disposed between the lower surface of the outer downward protruding portion 412 of the upper case 41 and the upper surface of the first impactor 43, and the second rubber ring 44 is disposed between the lower surface of the first impactor 43 and the upper surface of the double bent portion 453 of the second impactor 45 so that the air entering through the inlet 411 of the upper case 41 is prevented from leaking outward.

The outer upward protruding portion 454 of the second impactor 45 is protruded upward at or above the height at which the surface on which the upper case 41 and the first impactor 43 are in contact and the surface on which the first impactor 43 and the second impactor 44 (the upper surface of the double bent portion of the second impactor) are in contact can be sealed from the outside. The position at which the outer upward protruding portion 454 is bent upward from the double bent portion 453, that is, the position in the radial direction corresponds to the outer peripheral end portion of the upper case 41 and the first impactor 43.

The first trap 433 is formed to be deeper than the second trap 456 so that relatively large particles contained in the air entering through the inlet 411 of the upper case 41 can remain in the first trap 433.

The position at which the double bent portion 453 is bent upwardly is further radially outward than where the slots 432 of the first impactor 43 are disposed.

Figure 5:
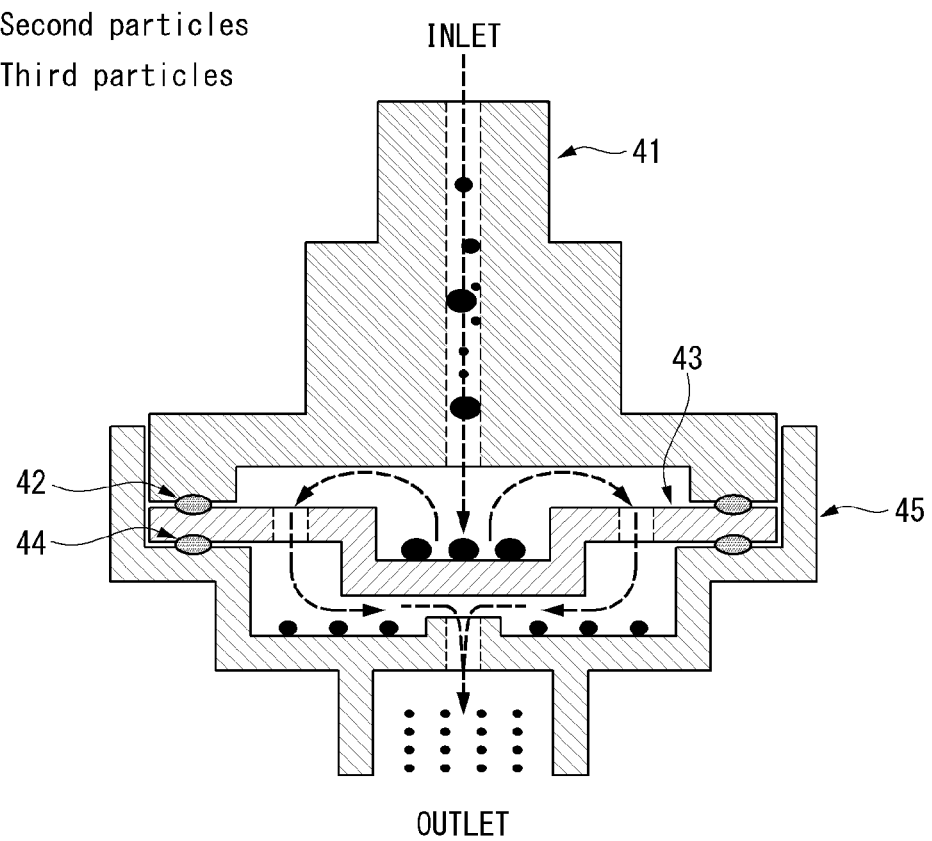
FIG. 5 illustrates the traveling path of dust particles entering the impactor assembly according to the present invention.

FIG. 5 illustrates the traveling path of dust particles entering the impactor assembly according to the present invention.

Air entering through the inlet 411 of the upper case 41 bumps against the upper surface of the central downward depression 431 of the first impactor 43 and bounces off. It is assumed that the air contains several particles of different sizes, for example first particles of the largest size, second particles of the middle size and third particles of the smallest size.

The first particles having the largest size among the particles struck on the upper surface of the central downward depression 431 of the first impactor 43 bounce off but do not exceed the depth of the first trap 433 and remain in the first trap 433. The second and third particles smaller than the first particle bounce off and pass through the slots 432 of the first impactor 43 while overcoming the depth of the first trap 433.

Particles flowing out of the slots 432 of the first impactor 43 bump against the upper surface of the second impactor 45 and the relatively large second particles do not exceed the depth of the second trap 456 and are trapped in the second trap 456. The third particles smaller than the second particles pass through the outlet 451 of the second impactor 45 while overcoming the depth of the second trap 456.

The particles passing through the outlet 451 of the second impactor 45 are guided by the guiding portion 455 so that they downwardly proceed toward a sensing unit without being bent outward.

This impactor assembly is mounted on an inlet port through which air is introduced into the dust sensor, so that only particles of a small size among the particles contained in the air can enter a sensor unit, and prevents external light from entering the dust sensor.

In the case of a photoelectric type dust sensor, only the light emitted from a light emitting element included in a sensing unit needs to enter a light receiving element included in the sensing portion, so that the detection capability of the light receiving element is increased. When external light such as natural light or fluorescent light enters the light receiving element, disturbance may occur and the accuracy of the sensing unit may deteriorate. However, since the impactor assembly according to the present invention can prevent external light from entering the inside of the dust sensor, the accuracy of the dust sensor can be improved.

Figure 6:
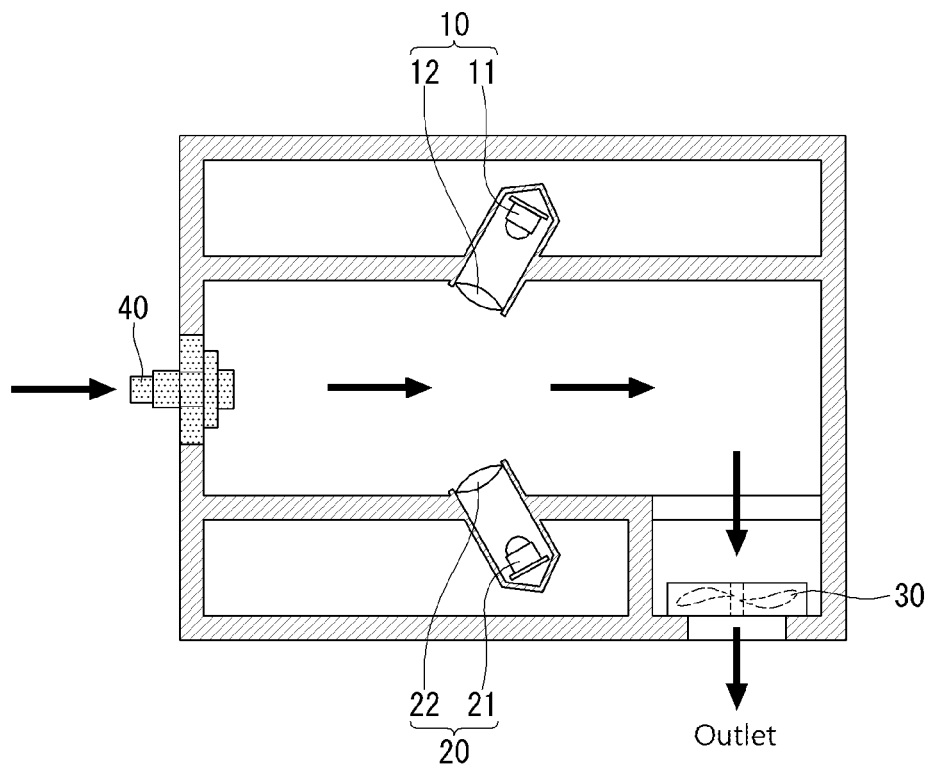
FIG. 6 is a schematic view showing an internal structure of a dust sensor employing an impactor according to the present invention.
Figure 7:
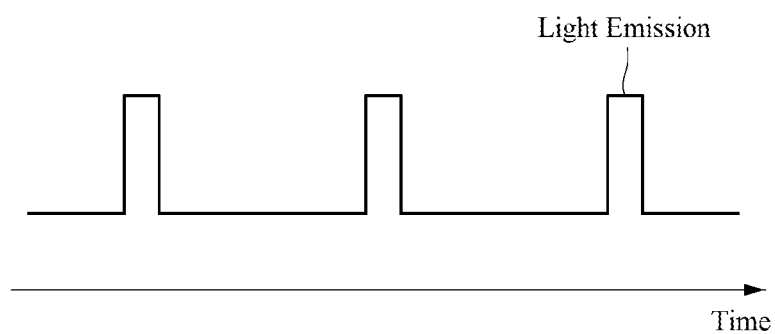
FIG. 7 shows optical pulses emitted from a light source of the dust sensor.
Figure 8:
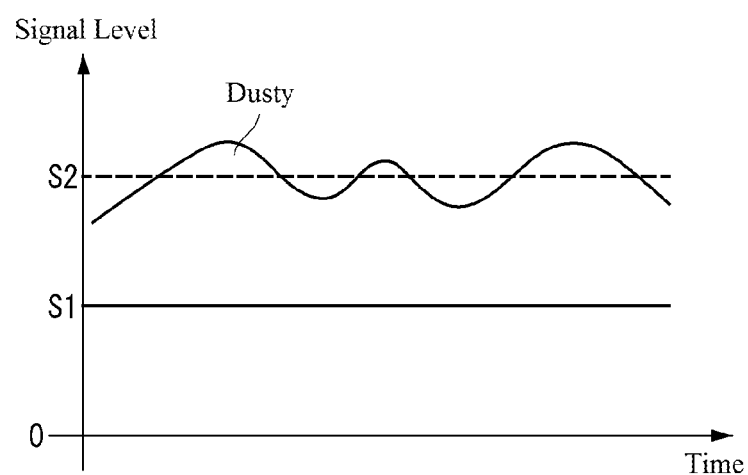
FIG. 8 shows signals output from a light receiving element of the dust sensor.

FIG. 6 is a schematic view showing an internal structure of a dust sensor employing an impactor according to the present invention, FIG. 7 shows optical pulses emitted from a light source of the dust sensor, and FIG. 8 shows signals output from a light receiving element of the dust sensor.

The dust sensor according to the present invention may comprise a light emitting unit 10 for emitting light in an air passage path inside the dust sensor, a light receiving unit 20 for collecting light scattered by dust contained in the air flowing through the air passage path, a fan 30 for generating a suction force for allowing air to flow into the air passage path, and an impactor assembly 40 for limiting the size of the particles contained in the air entering the dust sensor. The dust sensor may further comprise a maze (not shown) for confining a part of light radiated by the light emitting unit 10 and scattered from dust.

The dust sensor may further comprise a connector (not shown) for connecting a controller for controlling the operation of the dust sensor. The dust sensor receives control signals for driving the light emitting unit 10, the light receiving unit 20 and the fan 30 from the controller, and transmits output signals of the light receiving unit 20 to the controller.

The light emitting unit 10 may comprise a light source 11 for radiating light of a predetermined band and a source lens 12 for converting the light radiated by the light source 11 into parallel light. The light source 11 may be a laser diode LD or a light emitting diode LED. The source lens may be a collimating lens for converting diverging light into parallel light.

The light receiving unit 20 may comprise a light receiving element 21 for generating an electric signal proportional to the amount of incident light, and a receiving lens 22 for condensing incident light on the light receiving element 11.

The light emitting unit 10 radiates light to the air passage path. The light emitting unit 10 is mounted to be staggered with the traveling direction of the air so that no light radiated by the light emitting unit 10 is directly received by the light receiving unit 20 and dust contained in the air are not accumulated in the light emitting unit 10. That is, the light emitting portion 10 can be mounted obliquely toward the direction in which air flows out. In other words, the light emitting portion 10 may be mounted such that the direction in which the air travels and the direction in which the light emitted by the light emitting portion 10 travels are at an acute angle.

The light emitting unit 10, as shown in FIG. 7, radiates light in a periodic pulse shape. The light receiving unit 20 outputs, as shown in FIG. 8, converts the light incident on the light receiving element 21 into an electric signal and outputs the electric signal.

In the photoelectric type dust sensor, even if there is no dust in the air passage path, light radiated from the light emitting unit 10 is irregularly reflected in a main body and a small amount of light is received by the light receiving unit 20. So, as shown in FIG. 8, the level of the output signal of the light receiving element 21 has a constant value 51 even if there is no dust. The light receiving element 21 outputs a signal which changes in the form of a curve in FIG. 8 corresponding to the concentration of dust contained in the air passing through the air passage path.

The fan 30 is driven under the control of the controller to generate a suction force so that air flows at a constant speed or pressure in the air passage path. The fan may be disposed at the end of the air passage path, that is, near an air outlet. The fan may be omitted if air flows from the outside at a predetermined pressure.

The impactor assembly 40 filters the particles contained in the air entering the air passage path of the dust sensor and passes only small particles without passing large particles, so the sensing unit including the light emitting unit 10 and the light receiving unit 20 is not exposed to dust of all sizes. Accordingly, the dust sensor can accurately measure the concentration of the fine dust, and the contamination of the sensing unit by large particles can be reduced.

Throughout the description, it should be understood by those skilled in the art that various changes and modifications are possible without departing from the technical principles of the present invention. Therefore, the technical scope of the present invention is not limited to the detailed descriptions in this specification but should be defined by the scope of the appended claims.

What is claimed is:

1. An impactor assembly, comprising:
   an upper case equipped with an inlet which is formed through a center of the upper case and through which air is sucked, the upper case including an outer downward protruding portion protruding in a direction in which the air passing through the inlet and formed on an outer portion of a portion where the air that has passed through the inlet escapes;
   a first impactor including a central downward depression which is formed by sinking a center of a disk-shaped body of the first impactor, the first impactor being provided with a plurality of slots formed along a circumferential direction in an outer periphery of the central downward depression in a radial direction; and
   a second impactor equipped with an outlet at a center, the second impactor including a central upward protruding portion, a double-bent portion, an outer upward protruding portion and a guide portion,
   wherein the central upward protruding portion is protruded upward and has a larger outer diameter than the outlet,
   wherein the double-bent portion is formed by upwardly bending a disk-shaped body of the second impactor at a first position outer than the central upward protruding portion in the radial direction, and then outwardly bending the body of the second impactor,
   wherein the outer upward protruding portion is protruded upward while being bent from an end portion of the double-bent portion, and
   wherein the guide portion is protruded downward from a lower surface of the body of the second impactor at a position outer than the central upward protruding portion in the radial direction.

2. The impactor assembly of claim 1, further comprising:
   a first rubber ring disposed between a lower surface of the outer downward protruding portion and an upper surface of the first impactor; and
   a second rubber ring disposed between a lower surface of the first impactor and an upper surface of the double bent portion.

3. The impactor assembly of claim 1, wherein an outwardly extending portion of the double bent portion supports the first impactor and the upper case.

4. The impactor assembly of claim 1, wherein the outer downward protruding portion and the double bent portion are formed on an outer side of the plurality of slots in the radial direction.

5. The impactor assembly of claim 4, wherein the outer upward protruding portion is protruded upward at or above a height at which a surface on which the upper case and the first impactor are in contact is not exposed to outside.

6. The impactor assembly of claim 4, wherein the outer upward protruding portion is protruded upward at a position corresponding to outer peripheral end of the upper case and the first impactor in the radial direction.

7. The impactor assembly of claim 1, wherein an upper portion of the central downward depression is surrounded by an upper surface of the disk-shaped body of the first impactor to form a first trap, and largest particles among particles contained in the air flowing through the inlet are contained in the first trap.

8. The impactor assembly of claim 7, wherein a second trap is formed between the central upward protruding portion and the double bent portion to hold largest particles among particles contained in the air entering through the plurality of slots.

9. The impactor assembly of claim 8, wherein the first trap is formed to be deeper than the second trap.

10. A dust sensor, comprising:
    an impactor assembly for passing only relatively small particles among particles contained in air;
    a light emitting unit for radiating light in a path through which the air introduced through the impact assembly passes; and
    a light receiving unit for receiving light scattered from particles included in the air passing through the path,
    wherein the impactor assembly comprises:
    an upper case equipped with an inlet which is formed through a center of the upper case and through which air is sucked, the upper case including an outer downward protruding portion protruding in a direction in which the air passing through the inlet and formed on an outer portion of a portion where the air that has passed through the inlet escapes;
    a first impactor including a central downward depression which is formed by sinking a center of a disk-shaped body of the first impactor, the first impactor being provided with a plurality of slots formed along a circumferential direction in an outer periphery of the central downward depression in a radial direction; and
    a second impactor equipped with an outlet at a center, the second impactor including a central upward protruding portion, a double-bent portion, an outer upward protruding portion and a guide portion,
    wherein the central upward protruding portion is protruded upward and has a larger outer diameter than the outlet,
    wherein the double-bent portion is formed by upwardly bending a disk-shaped body of the second impactor at a first position outer than the central upward protruding portion in the radial direction, and then outwardly bending the body of the second impactor, wherein the outer upward protruding portion is protruded upward while being bent from an end portion of the double-bent portion, and wherein the guide portion is protruded downward from a lower surface of the body of the second impactor at a position outer than the central upward protruding portion in the radial direction.

* * * * *